US00PP12029P2

(12) United States Plant Patent
Heims

(10) Patent No.: US PP12,029 P2
(45) Date of Patent: Jul. 31, 2001

(54) XHEUCHERELLA PLANT NAMED 'VIKING SHIP'

(75) Inventor: Dan M. Heims, Portland, OR (US)

(73) Assignee: Terra Nova Nurseries, Inc., Tigard, OR (US)

( * ) Notice: Subject to any disclaimer, the term of this patent is extended or adjusted under 35 U.S.C. 154(b) by 0 days.

(21) Appl. No.: 09/324,626

(22) Filed: Jun. 2, 1999

(51) Int. Cl.[7] ..... A01H 5/00
(52) U.S. Cl. ..... Plt./263
(58) Field of Search ..... Plt./263

(56) References Cited

PUBLICATIONS

UPOV CD–ROM Heucherella named 'Viking Ship', QZ, PBR 000479, 2000.*

* cited by examiner

*Primary Examiner*—Bruce R. Campell
*Assistant Examiner*—Melissa L. Kimball
(74) *Attorney, Agent, or Firm*—Klarquist Sparkman Campbell Leigh & Whinston, LLP

(57) ABSTRACT

A new and distinct hybrid of xHeucherella characterized by distinctive spring foliage and unusual flowers.

2 Drawing Sheets

The present invention relates to a new and distinct bigeneric hybrid of Heuchera and Tiarella in the Saxifrage family (Saxifragaceae), which originated as a cross-pollination of a Tiarella (select pink seedling) (pollen parent) (unpatented) and Heuchera 'Green Spice' (pod parent) (unpatented).

The new xHeucherella is the result of a controlled cross of the aforementioned plants at Terra Nova Nurseries, Inc., in Canby, Oreg. This hybrid was selected from a small selection of resultant seedlings. Mother plants were retained to observe habit and to compare with their progeny. The new variety has been reproduced only by asexual propagation (division and tissue culture). Each of the progeny exhibits identical characteristics to the original plant and is unlike any xHeucherella offered by any American nursery or book, known to the inventor, as evidenced by the following characteristics:

1. Spring formation of extremely cut leaves in an unusual boat-and-oars pattern (later described) results in the leaf surface being restricted to the width of the vein for a section of the leaf, terminated in a leaflet;
2. Unusual pink flowers.

Asexual propagation by division and tissue culture as done in Tigard, Oreg., shows that the foregoing characteristics and distinctions come true to form and are established and transmitted through succeeding propagations. The present information has not been evaluated under all possible environmental conditions. The phenotype may vary with variations in environment without a change in the genotype of the plant.

BRIEF DESCRIPTION OF THE PHOTOGRAPHS

DETAILED PLANT DESCRIPTION

Figure 1:
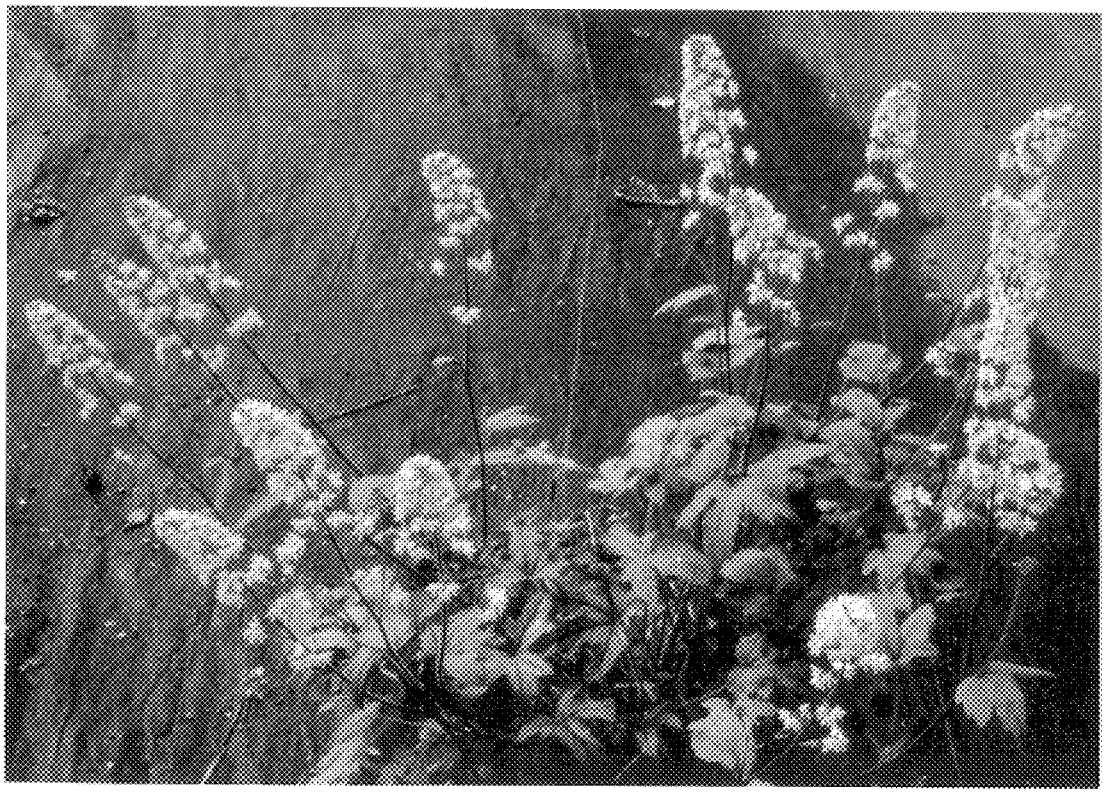
FIG. 1 is an example of spring growth and bloom.
Figure 2:
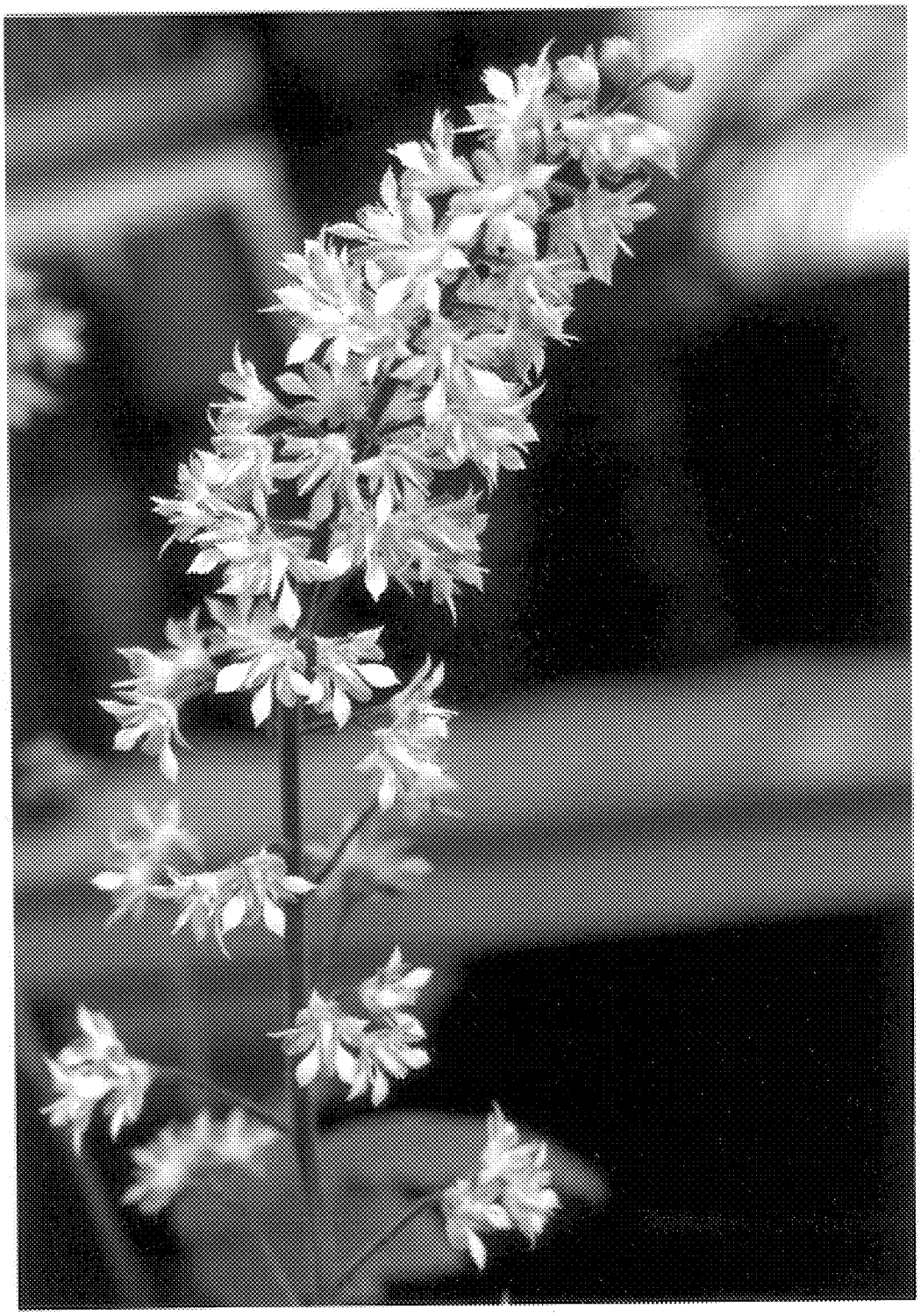
FIG. 2 is a close-up showing the flower in detail.

The following is a detailed description of the new xHeucherella hybrid based on observations of specimens in Canby, Oreg. The color descriptions are all based on The Royal Horticultural Society Colour Chart. Reference to spring and summer foliage is only with regard to leaf shape and no other morphological or color characteristics.

Foliage:

*Type.*—Evergreen in USDA zones 6 to 8. Deciduous in zones 4 and 5.
*Shape.*—Palmate, 5–7-lobed, central lobe is elongated and tapers to a fine point. Spring foliage is exceedingly cut to vein width with expanded leaflets (oar-like appendages), which differs from the undivided summer foliage (second flush of leaves emerging in May).
*Length.*—7–8 cm. (2.75–3.25 in.).
*Width.*—8–9 cm. (3–3.75 in).
*Petiole length.*—9–11 cm (3.5–4.25 in).
*Margins.*—Serrate to dentate, ciliolate.
*Apex.*—Acute.
*Base.*—Cordate.
*Texture.*—Upper surface smooth, slightly pubescent, smooth below.
*Leaf arrangement.*—Basal clump.
*Venation.*—Reticulate.

Flower:

*Fertility.*—Sterile, no seed set, no pollen evident.
*Fragrance.*—None noted.
*Petal count.*—5 petals, 5 calyx lobes.
*Bracts.*—2–4 bracts similar to foliage but greatly reduced. (to 95%).
*Petal shape.*—Triangular, stellate.
*Flower type.*—Calyx tube campanulate, ovary superior, stamens barren.
*Carpel number.*—2.
*Stamen number.*—7–10.
*Flower size.*—To 1 cm from petal tip to petal tip.
*Inflorescence type.*—Panicle.
*Peduncle width.*—3 mm tapering to 1 mm (pedicels).
*Panicle height.*—47 cm.
*Bloom period.*—April through July, repeating sporadically in fall.
*Lastingness.*—3–4 days (individual blooms on the plant). 7–14 days (individual panicles on the plant).

Size (1.5-year-old plant grown in the ground in Canby, Oreg.):

*Height.*—16 cm.

*Spread.*—32 cm.

Disease: None observed on plants grown commercially in Canby, Oreg.

Color characteristics:

*Foliage.*—Upper surface, between veins (overlay): RHS Green Group 138B. Upper surface, along veins: RHS Green Group 137A–B. Upper surface, markings: RHS Brown Group 200A. Lower surface: RHS Green Group 138A–B.

*Flowers.*—Calyx and lobes, RHS White Group 155B; petals, RHS Red Group 39C; inside and outside same color.

*Peduncle and pedicel.*—RHS 148A Yellow-Green Group becoming RHS 185A–B Greyed-Purple Group (upper quarter of inflorescence, including pedicels).

DESCRIPTION OF PARENT PLANTS

This Heuchera hybrid has characteristics that make it unique from it parents. One parent was a selected pink Tiarella seedling, having cut green foliage and pink flowers. The other parent was Heuchera 'Green Spice', a cultivar bearing tall green flowers and silvered foliage with purple veins. xHeucherella "Viking Ship" has cut green leaves with a silvery-green overlay and large, branched flowers of the xHeucherella type, which are unlike either parent.

I claim:

1. A new and distinct hybrid of xHeucherella plant substantially as shown and described, characterized by its unique foliage and branched pink flowers.

* * * * *